United States Patent [19]

Kuroda et al.

[11] Patent Number: 4,627,915
[45] Date of Patent: Dec. 9, 1986

[54] ABSORBENT OF AUTOANTIBODY AND IMMUNE COMPLEXES, ADSORBING DEVICE AND BLOOD PURIFYING APPARATUS COMPRISING THE SAME

[75] Inventors: Toru Kuroda; Naokuni Yamawaki, both of Fuji, Japan

[73] Assignee: Asahi Kasei Kogyo Kabushiki Kaisha, Osaka, Japan

[21] Appl. No.: 592,631

[22] Filed: Mar. 23, 1984

[30] Foreign Application Priority Data

Apr. 6, 1983 [JP] Japan .................................. 58-59197
Apr. 6, 1983 [JP] Japan .................................. 58-59199

[51] Int. Cl.$^4$ ............................................. B01D 15/00
[52] U.S. Cl. .................................. 210/195.2; 210/434; 210/927
[58] Field of Search ............ 210/632, 638, 927, 433.2, 210/434, 195.2, 321.1; 260/112 B

[56] References Cited

U.S. PATENT DOCUMENTS

| | | | |
|---|---|---|---|
| 4,243,532 | 1/1981 | Tsuda et al. | 210/927 X |
| 4,375,414 | 3/1983 | Strahilevitz | 210/638 |
| 4,384,954 | 5/1983 | Nakashima et al. | 210/927 X |
| 4,421,684 | 12/1983 | Nakashima et al. | 210/927 X |
| 4,490,290 | 12/1984 | Gani et al. | 210/927 X |

Primary Examiner—Frank Spear
Attorney, Agent, or Firm—Sprung Horn Kramer & Woods

[57] ABSTRACT

An adsorbent for adsorbing thereonto an autoantibody and/or immune complexes from a body fluid. The adsorbent comprises a surface, a hydrophobic member and a negative charge-producing member. The negative charge-producing member is adapted to produce such an effective number of negative charges in a body fluid that the ratio of:

$$\frac{\text{Effective number of negative charges}}{\text{Number of hydrophobic members}}$$

is greater than 1. The adsorbent is excellent in selectively and efficiently adsorbing an autoantibody and/or immune complexes while little adsorbing useful substances from the body fluid. The adsorbent may be used in an adsorbing device comprising a vessel having a fluid inlet and a fluid outlet with the adsorbent contained in the vessel. The adsorbing device may be used in a blood purifying apparatus for adsorbing and removing an autoantibody and/or immune complexes from blood plasma, which apparatus comprises a blood circulation passage provided with a plasma separating means and a blood-plasma mixing means, and a plasma recycle passage connected to the blood circulation passage and adapted to introduce plasma, separated by the plasma separating means and purified by a plasma purifying means comprised of the above-mentioned adsorbing device and disposed in the plasma recycle passage, into the mixing device.

16 Claims, 6 Drawing Figures

ABSORBENT OF AUTOANTIBODY AND IMMUNE COMPLEXES, ADSORBING DEVICE AND BLOOD PURIFYING APPARATUS COMPRISING THE SAME

This invention relates to an adsorbent of autoantibody and immune complexes, and an adsorbing device and blood purifying apparatus each comprising the same. More particularly, this invention is concerned with an adsorbent useful for effectively and selectively adsorbing and removing an autoantibody and/or immune complexes, which adsorbent comprises a surface and, linked with the surface, at least one hydrophobic member and further, linked with the surface or the hydrophobic member or with the both, at least one negative charge-producing member. The present invention is also concerned with an efficient adsorbing device for autoantibody and/or immune complexes from a living body fluid (hereinafter referred to simply as "body fluid") and an efficient blood purifying apparatus for adsorbing and removing an autoantibody and/or immune complexes from blood plasma, which adsorbing device and blood purifying apparatus each comprises the above-mentioned adsorbent.

It is generally believed that an autoantibody and immune complexes found in the body fluid, e.g. blood, have a close relationship with the cause or advance of cancer, immune proliferative syndrome, autoimmune diseases (such as rheumatoid arthritis and systemic lupus erythematodes), and immune reactions (such as allergic reaction or rejection at a transplantation of an internal organ). Accordingly, there has been an ever-increasing demand for an adsorbent which can effectively and selectively adsorb thereonto an autoantibody and immune complexes from a body fluid such as blood and plasma thereby to prevent the advance of the above diseases and undesirable immune reactions, relieve the symptoms thereof and expedite the cure of the patients.

In line with the efforts to develop such a desirable adsorbent, there have been proposed various adsorbents, including an immune adsorbent comprising protein A fixed to an insoluble carrier [see Terman D. S. et al, J. Immunol., 124, 795 (1980); New England J. Med., 305, 1195 (1981)], an acrylic acid ester type porous resin [for example, XAD-7 supplied by Rohm and Haas Co., U.S.A.; see Agishi T., Zinko Zoki, 9, 264 (1980)] and a cation exchange member, such as carboxymethyl cellulose [Johnson L. D. et al, Can. J. Biochem. 42, 795 (1964)]. These adsorbents have, however, various problems which limit their applications. The immune adsorbent comprising protein A fixed to an insoluble carrier has a specific adsorbing capacity for an immunoglobulin and/or immune complexes, but, since protein A is a biologically active protein derived from yellow staphylococcus, this immune adsorbent is disadvantageous in that the starting material is difficult to obtain and the manufacturing cost is high. Furthermore, since the adsorbent is unstable, deactivation thereof is readily caused by the handling at the fixing step or during the storage after the fixing step. Moreover, when this immune adsorbent is used in the state where it is kept in contact with the body fluid, there is a risk of trouble occurring through the elution of protein A. Still further, it is very difficult to sterilize this immune adsorbent while preventing deactivation. The acrylic acid ester type porous resin and the cation exchange member such as carboxymethyl cellulose are insufficient in adsorbing capacity and adsorption specificity. Moreover, since they even adsorb albumin from the body fluid, an abnormal change in the osmotic pressure is caused and they cannot be used safely as a curing means.

With a view to obviating the above drawbacks, it was proposed in European Patent Application Laid-Open Specification No. 56 977, which was published on Aug. 4, 1982, to use an adsorbing material for an autoantibody and/or immune complexes, which comprises (a) an insoluble carrier and (b) an organic low molecular weight compound containing a hydrophobic compound having a solubility of not more than 100 millimoles in one dl of a physiological saline solution at 25° C., said organic low molecular weight compound being fixed to the insoluble carrier. The organic low molecular weight compound has a special chemical structure which permits the compound to exhibit specific chemical interaction with the substances to be adsorbed. According to the disclosure, the adsorbent is capable of adsorbing an autoantibody and/or immune complexes at a high selectivity and high efficiency with minimal disadvantageous concurrent adsorption of useful substances. Further, according to the disclosure, it can be safely employed and readily sterilized thereby to render it suitable for the purification of body fluid. Investigations have been made on the adsorbing materials, as disclosed in the above-mentioned European Patent Application Laid-Open Specification No. 56977, which exhibit specific interaction with the substances to be adsorbed. Such investigations have led to the present invention. Hence, the present invention relates to an improvement of the adsorbent as disclosed in European Patent Application Laid-Open Specification No. 56977.

The desired properties of the materials to be employed for purifying a body fluid are as follows:

(1) They are capable of adsorbing thereonto an autoantibody and/or immune complexes at a high selectivity and high efficiency;
(2) Adsorption of the substances other than those intended is zero or very little;
(3) They do not activate the coagulation fibrinolysis system and complement system;
(4) They can be subjected to sterilization; and
(5) Their mechanical strength is sufficient.

We have made extensive and intensive studies with a view to providing an adsorbent of autoantibody and immune complexes which is improved over any of the adsorbents known in the art with respect to the above-described properties, especially items (1) and (2) above. The invention disclosed in European Patent Application Laid-Open Specification No. 56977 relates to an adsorbent of autoantibody and/or immune complexes comprising an insoluble carrier and an organic low molecular weight compound containing a hydrophobic molecule which is fixed to the insoluble carrier. The invention suggests that the hydrophobic property of the organic low molecular weight compound fixed to the carrier plays an important role in adsorbing an autoantibody and/or immune complexes. As a result of further studies, the present inventors have found that adsorption of an autoantibody and/or immune complexes and non-adsorption of the substances other than those intended are markedly improved by incorporating, at specific proportions, a negative charge-producing member in addition to the above-mentioned hydrophobic compound fixed to the surface of the adsorbent. Based on this novel finding, we have completed this invention.

It is, therefore, an object of the present invention to provide and adsorbent for adsorbing an autoantibody and/or immune complexes at an improved selectively and improved efficiency. Another object of the present invention is to provide an adsorbing device for autoantibody and/or immune complexes from a living body fluid, and a further object of the present invention is to provide a blood purifying apparatus for adsorbing and removing an autoantibody and/or immune complexes from blood plasma.

The foregoing and other objects, features and advantages of the present invention will be apparent to those skilled in the art from the following detailed description and appended claims taken in connection with the accompanying drawings in which:

Figure 1:
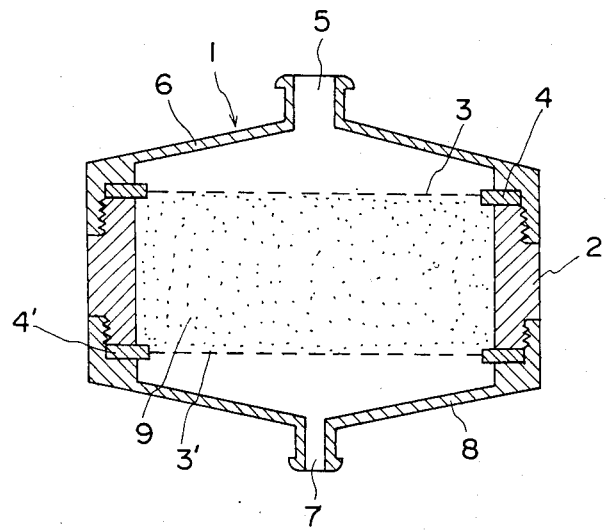
FIG. 1 is a sectional view illustrating one embodiment of the device for adsorbing an autoantibody and immune complexes according to the present invention.
Figure 2:
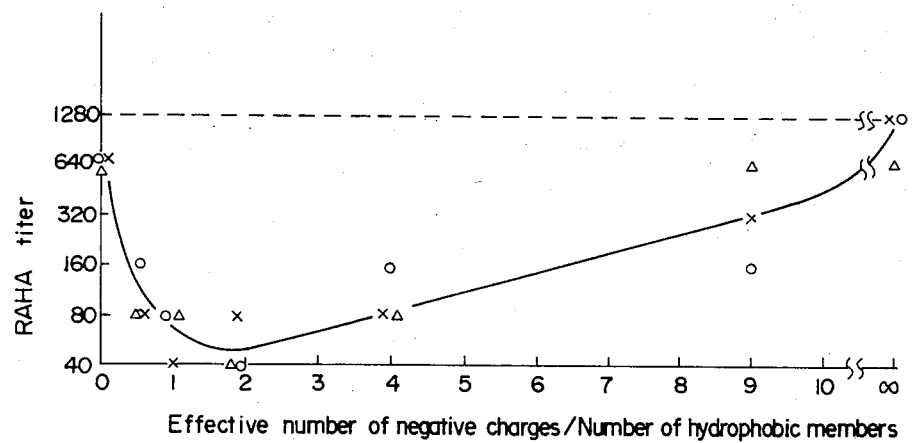
FIG. 2 shows the relationship between RAHA titer and effective number of negative charges/number of hydrophobic members, explained with reference to Example 3, a dashed line representing a value before adsorption and a solid line representing a value after adsorption.
Figure 3:
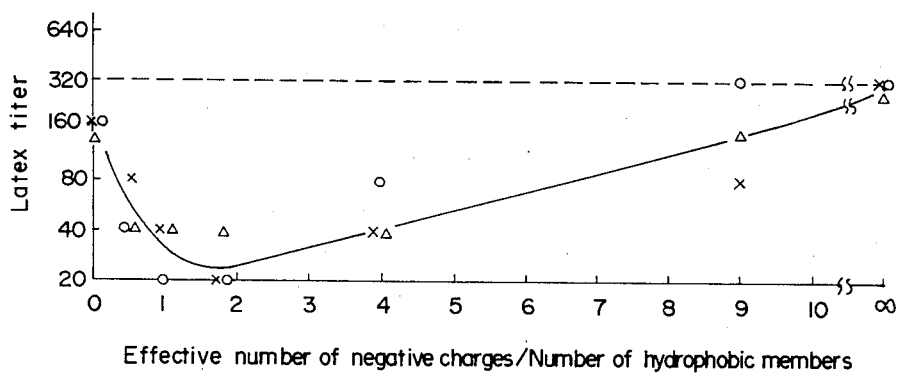
FIG. 3 shows the relationship between latex titer and effective number of negative charges/number of hydrophobic members.
Figure 4:
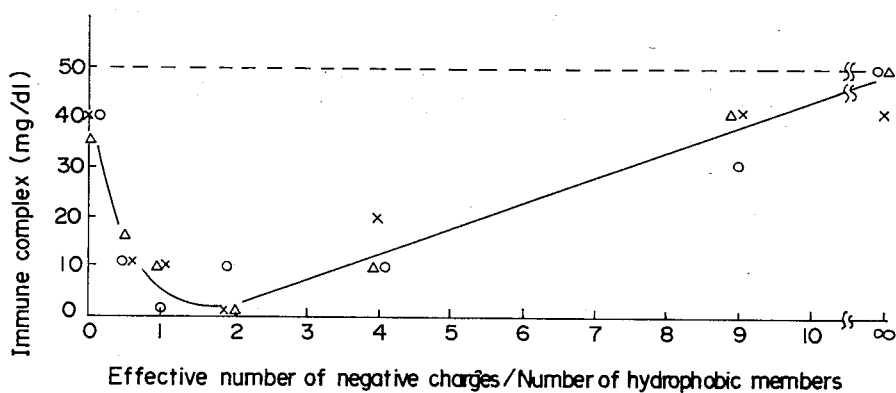
FIG. 4 shows the relationship between immune complex (mg/dl) and effective number of negative charges/number of hydrophobic members.
Figure 5:
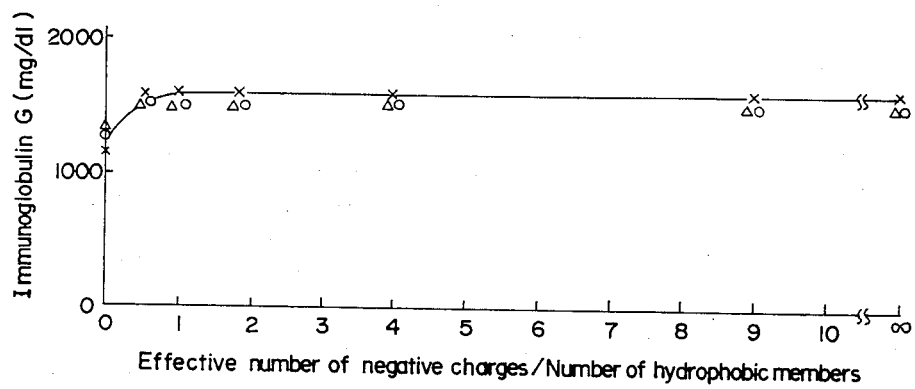
FIG. 5 shows the relationship between immunoglobulin G (mg/dl) and effective number of negative charges/number of hydrophobic members.
Figure 6:
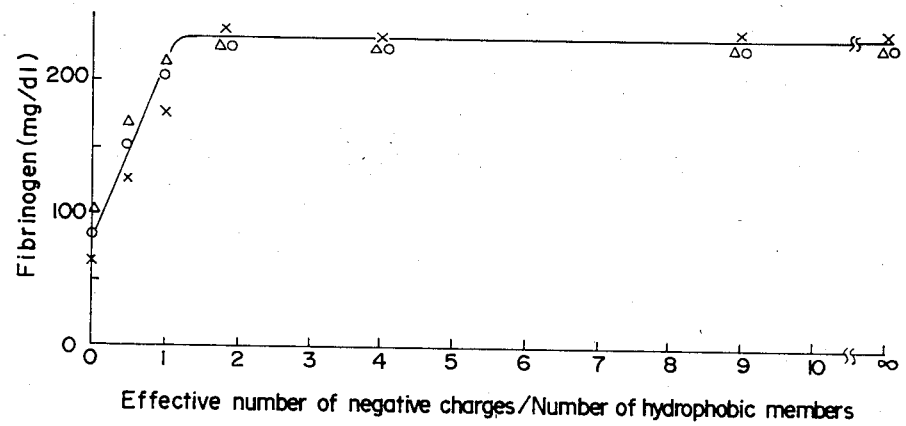
FIG. 6 shows the relationship between fibrinogen (mg/dl) and effective number of negative charges/number of hydrophobic members.

In one aspect of the present invention, there is provided an adsorbent for adsorbing thereonto an autoantibody and/or immune complexes from a body fluid, which comprises a surface and, linked with the surface, at least one hydrophobic member having 6 to 700 carbon atoms and further, linked with the surface or with the hydrophobic member or with the both, at least one negative charge-producing member having no carbon atom or having 1 to 5 carbon atoms, said negative charge-producing member being adapted to produce such an effective number of negative charges in a body fluid that the ratio of:

$$\frac{\text{Effective number of negative charges}}{\text{Number of said hydrophobic members}}$$

is greater than 1.

The hydrophobic member having 6 to 700 carbon atoms (hereinafter often referred to simply as "hydrophobic member") to be employed in the present invention may be a hydrophobic organic compound having 6 to 700 carbon atoms and having a molecular weight preferably not exceeding $10^4$, more preferably not exceeding $10^3$. The term "hydrophobic" as used herein indicates the property of lacking an affinity for, repelling, or failing to adsorb water. Among many hydrophobic members having 6 to 700 carbon atoms, aromatic ring compounds are preferred.

Any of the compounds having aromatic properties may be suitably employed. However, as the preferred compounds for obtaining good results, there may be mentioned aromatic compounds having a benzene ring or fused benzene ring such as benzene, naphthalene and phenanthrene; compounds having a oxygen-containing aromatic ring such as dibenzofuran, chromene and benzofuran; compounds having a sulfur-containing aromatic ring such as thianaphthene and thianthrene; compounds having a nitrogen-containing 6-membered ring such as phenanthridine, quinoline and acridine; and compounds having a nitrogen-containing 5-membered ring such as indole and carbazole. Among these aromatic compounds, those having a benzene ring or fused benzene ring are most preferable.

The hydrophobic member to be employed in the present invention has 6 to 700 carbon atoms. Specifically, from the viewpoint of improving the adsorbing capacity of autoantibody and/or immune complexes, the number of carbon atoms constituting the member may be preferably 6 or more, more preferably 10 or more, when the member contains an unsaturated bond therein. On the other hand, when the member contains single bonds alone, the number of carbon atoms may be preferably 10 or more, more preferably 15 or more. The upper limit of the number of carbon atoms is 700. The molecular weight of a compound having 700 carbon atoms is about 10,000. When a compound having a molecular weight of about 10,000 or more is detached and leaked into the body fluid such as blood, it may exhibit unfavorable antigenicity. From this viewpoint, the upper limit of the number of carbon atoms is set at 700. However, it is generally preferred that the number of carbon atoms do not exceed 500, especially 50.

With respect to the hydrophobic member to be employed in the present invention, those having a hydrophobic substituent such as chlorine and iodine exhibit an improved adsorbing capacity for an autoantibody and/or immune complexes as compared with those having no substituent. On the other hand, the members having multiple undissociable hydrophilic substituents such as a hydroxyl group, thiol group and amide group exhibit a decreased adsorbing capacity for an autoantibody and/or immune complexes as compared with those having no substituent. Hence, it is preferred that the number of undissociable hydrophilic substituents may be less than 1 per two carbon atoms constituting the hydrophobic member, especially less than 1 per three carbon atoms as mentioned above. This is possibly because the type of carbon linkage and the kind of substituent have significant effect on the mutual hydrophobic interaction between the adsorbent and the substances to be adsorbed.

The negative charge-producing member to be employed in the present invention has no carbon atom or 1 to 5 carbon atoms. It may comprise a group such as a carboxyl group, sulfo group, phosphono group, arsono group, phosphinico group, selenino group or the like and produces a negative charge in a body fluid such as blood. It is preferred that the molecular weight of the negative charge-producing member may be 10,000 or less, especially 1000 or less. As the suitable negative charge-producing member, there may be mentioned, for example, aliphatic amino acids such as glycine, alanine and aspartic acid, fatty acids such as $\gamma$-amino-n-butyric acid and $\epsilon$-amino-caproic acid, sulfamic acid, taurine and carbamyl phosphate.

In the present invention, each of the hydrophobic member and the negative charge-producing member may be separately present on the surface of the adsorbent. Alternatively, the negative charge-producing member may form a substituent of the hydrophobic member. It may be preferable that the negative charge-producing member be linked with the hydrophobic member as a substituent thereof, the number of said negative charge-producing members per hydrophobic member being 2 or more. Examples of the hydrophobic members having a negative charge-producing member as its substituent are aromatic ring compounds having two or more negative charge-producing substituents such as benzenedisulfonic acid and naphthalenedicarboxylic acid, and long chain aliphatic compounds having two or more negative charge-producing substituents such as succinocanavanine, polyglutamic acid and polyaspartic acid. Any of the above-mentioned aromatic ring compounds may be used advantageously. However, to better attain the objective of the present invention, it may be preferable to employ aromatic ring compounds having two or more negative charge-producing substituents, said aromatic ring compounds being selected from the class consisting of compounds having a benzene or fused benzene ring such as benzene, naphthalene and phenanthrene; compounds having an oxygen-containing aromatic ring such as dibenzofuran, chromene and benzofuran; compounds having a sulfur-containing aromatic ring such as thianaphthene and thianthrene; compounds having a nitrogen-containing 6-membered ring such as phenanthridine, quinoline and acridine; and compounds having a nitrogen-containing 5-membered ring such as indole and carbazole. Among them, the compounds comprising a benzene or fused benzene ring which respectively have two or more negative charge-producing substituents give especially good results.

In the present invention, also, an adsorbent comprising a hydrophobic member, to which a negative charge-producing substituent is attached, and a negative charge producing-member having no carbon atom or 1 to 5 carbon atoms may exhibit desirable adsorption performance in view of the objective to the present invention.

The term "number of carbon atoms" employed herein for defining the hydrophobic member and negative charge-producing member means the number of carbon atoms contained in the respective member but excluding the carbon atoms of any carboxyl groups. The reason for excluding the carbon atoms of any carboxyl groups is that the carboxyl group is hydrophilic and generally exhibits a negative charge effective only. With respect to the other groups than the carboxyl group such as an alkoxyl group, aldehyde group, alkoxycarbonyl group and the like, all of the carbon atoms thereof are counted.

The adsorbent of the present invention has at least one negative charge-producing member which is adapted to produce such an effective number of negative charges in a body fluid that the ratio of:

$$\frac{\text{Effective number of negative charges}}{\text{Number of hydrophobic members}}$$

is greater than 1. If the ratio is 1 or less, adsorption of fibrinogen and complement components (C3c, C4 etc.) which are substances not to be adsorbed disadvantageously increases, while the surface area available for adsorbing the intended substances decreases thereby to decrease adsorption of an autoantibody and immune complexes. The ratio may be generally in the range of 1.1 to 10, preferably in the range of 1.2 to 5, more preferably in the range of 1.3 to 3.

The term "effective number of negative charges" as used herein means the number of negative charges produced on the negative charge-producing members when in a body fluid or, in the event that positive charges are concurrently produced on the negative charge-producing members when in a body fluid, the number of negative charges minus the number of positive charges.

In the present invention, the number of hydrophobic members linked with the surface of a carrier or the like may be in the range of generally 1 $\mu$mol to 1 mmol, preferably 10 $\mu$mol to 500 $\mu$mol, more preferably 50 $\mu$mol to 300 $\mu$mol, per ml of the carrier or the like.

It is assumed that a hydrophobic interaction (van der Waals force) is exerted between the carbon atoms attributed to the hydrophobic member and an autoantibody and/or immune complexes. Moreover, Coulomb force presumably occurs between the negative charge-producing member and the positive charges of an autoantibody and/or immune complexes. Presumably due to the addition of the Coulomb force to the hydrophobic interaction, the non-specific adsorption of useful proteins of the adsorbent is decreased by the Coulomb force, and the capacity of the adsorbent for adsorbing an autoantibody and/or immune complexes is increased as much as the decrease of the non-specific adsorption of useful proteins. Accordingly, the adsorption of an autoantibody and/or immune complexes of the adsorbent of the present invention is advantageously high and the non-specific adsorption of useful proteins of the adsorbent of the present invention is advantageously low.

As mentioned hereinbefore, it is preferred that the respective molecular weight of the hydrophobic member and negative charge-producing member to be employed in the present invention do not exceed 10,000, especially do not exceed 1000, to avoid the unfavorable antigenicity that may occur when they are detached and leaked into the body fluid, such as blood.

The process for preparing the adsorbent of the present invention is not critical, and there may be employed, for example, a customary method for preparing an adsorbent for affinity chromatography which includes activating a carrier and linking a ligand therewith. An illustrative explanation of the method will be given below.

As the suitable carrier, there may be employed any carrier which is capable of linking therewith a negative charge-producing member having no carbon atom or having 1 to 5 carbon atoms and a hydrophobic member having 6 to 700 carbon atoms. The carrier may be hydrophilic or hydrophobic. In some cases, however, a hydrophilic carrier is preferred, since undesirable concurrent adsorption of albumin sometimes occurs onto the adsorbent when a hydrophobic carrier is used.

As the suitable carrier, there may be mentioned any carrier which is insoluble in a body fluid. The form of the insoluble carrier is not particularly critical, and any of a number of known forms may be used. For example, there may be used particulate, fibrous, hollow fibrous and filmy forms. Among these forms, particulate, especially spherically particulate, and fibrous forms are preferred from the viewpoints of facilitating the handling of the resulting adsorbent and increasing the amount of the hydrophobic member and negative charge-producing member that are linked with the carrier.

In the case of a particulate carrier, it is preferred that the average particle size thereof be in the range of 25 to 2,500 microns, especially 50 to 1500 microns. The specific surface area of the carrier may be preferably 5 m²/g or more, more preferably 55 m²/g or more, in the dry state.

As the suitable particulate carrier, there may be mentioned agarose, dextran, cellulose, polyacrylamide, glass, silica and activated charcoal. Hydrophilic carriers having a gel structure generally give good results. Any of the known carriers customarily employed for fixation of enzymes or affinity chromatography can be used without any particular limitation.

The particulate carrier may be porous. In particular, it may be composed of a porous polymer. In the present invention, it is necessary that the particulate porous polymer be capable of being linked with a negative charge-producing member having no carbon atom or 1 to 5 carbon atoms and a hydrophobic member having 6 to 700 carbon atoms. The molecular weight exclusion limit (protein) of the porous polymer may preferably be in the range of 150,000 to 10,000,000, since the molecular weight of the substances to be adsorbed ranges from 150,000 in the case of IgG to 10,000,000 in the case of immune complexes, especially IgM immune complex. The molecular weight exclusion limit of the porous polymer may more preferably be in the range of 1,000,000 to 5,000,000.

As the suitable polymer, there may be mentioned polyamides, polyesters, polyurethanes, vinyl compound polymers and other known polymers capable of having a porous structure. Especially, a particulate porous polymer of a vinyl compound which has been rendered hydrophilic with a hydrophilic monomer is preferred.

As the material of the carrier, there may be preferably used a hydroxyl group-containing crosslinked copolymer, and especially good results can be obtained when a crosslinked copolymer, comprising vinyl alcohol units as the main constituent, is used as the carrier.

Crosslinked polymers, comprising vinyl alcohol units as the main constituent, can be synthesized by the polymerization of a hydroxyl group-containing monomer or the introduction of hydroxyl groups into a polymer by a chemical reaction. Both the processes may be adopted in combination. The radical polymerization process may be used for the polymerization. A crosslinking agent may be introduced by copolymerization at the polymerization step or by chemical reaction of a polymer (reaction between polymers or reaction of a polymer with a crosslinking agent).

In the case of a fibrous carrier, it is preferred that the diameter of the fiber be in the range of 0.02 to 10 denier, especially 0.1 to 5 denier. When the diameter of the fiber is too large, the amount of linked globulin compounds and the adsorption speed thereof are disadvantageously decreased. On the other hand, when the diameter of the fiber is too small, various drawbacks such as activation of the coagulation system, adhesion of hematocytes and clogging of the adsorbent are liable to occur. As the suitable fibrous carrier, there may be mentioned those of regenerated cellulose fibers, nylon fibers, acrylic fibers, polyester fibers and other known fibers.

Each of the hydrophobic member and negative charge-producing member may be linked with a surface by any of the known methods such as covalent bonding, ionic bonding, physical adsorption, embedding, insolubilizing precipitation onto the polymer surface and the like. From the viewpoint of preventing the elution of members linked with the surface, it is preferred that their fixation and insolubilization be effected by covalent bonding. For this purpose, the customary techniques for activating a carrier and bonding a ligand that have been generally used for fixation of enzymes and affinity chromatography may be employed in the present invention.

As the suitable carrier activation method to be employed in the present invention, there may be mentioned, for example, a cyanogen halide method, epichlorohydrin method, bisepoxide method, triazine halide method, bromoacetyl bromide method, ethyl chloroformate method and 1,1'-carbonyldiimidazole method. The carrier activation method to be employed in the present invention is not limited to the above, if it provides on the carrier a reaction site which can effect a substitution reaction and/or addition reaction with an active hydrogen-containing nucleophilic group such as an amino group, hydroxyl group, carboxyl group and thiol group contained in a compound to be converted to the hydrophobic member or negative charge-producing member. From the viewpoints of chemical stability and thermal stability, a method using an epoxide, especially epichlorohydrin, is preferred.

There has been described above the process in which a carrier is activated and then a negative charge-producing member having no carbon atom or having 1 to 5 carbon atoms and a hydrophobic member having 6 to 700 carbon atoms are linked with the carrier. However, the process for producing the adsorbent of the present invention is not limited to the above process. For example, there may be adopted a method in which a negative charge-producing member and hydrophobic member are bonded with a polymerizable monomer and/or crosslinking agent and then the monomer and crosslinking agent having the negative charge-producing member and hydrophobic member bonded therewith is subjected to polymerization (copolymerization), or another method in which a crosslinked polymer in the form of particles is postcured with a crosslinking agent having a negative charge-producing member and hydrophobic member bonded therewith. Moreover, there may be adopted a further method in which an insoluble material is coated with a polymer which can be bonded with a negative charge-producing member and hydrophobic member and then the polymer coated on the material is bonded with the negative charge-producing member and hydrophobic member, or a still further method in which a polymer is bonded with a negative charge-producing member and hydrophobic member and then the polymer is coated on an insoluble material. In this case, the coated polymer may be postcured according to need. Furthermore, there may be adopted an additional method in which a negative charge-producing member and hydrophobic member are activated and then the activated members are bonded with a carrier, or an even further method in which a hydrophobic member is linked with a carrier having a negative charge-producing member. Illustratively stated, the adsorbent according to the present invention exhibits its advantageous effect when it is in such a state that a negative charge-producing member having no carbon atom or having 1 to 5 carbon atoms and a hydrophobic member having 6 to 700 carbon atoms are, at specific proportions, observed over the surface of the adsorbent. Hence, as stated above, a variety of processes can be adopted for producing the adsorbent of the present invention.

For advantageous use of the adsorbent according to the present invention, it may be packed in a vessel having a body fluid inlet and a body fluid outlet. Hence, in another aspect of the present invention, there is provided an adsorbing device for an autoantibody and/or immune complexes from a body fluid, which comprises a vessel having a fluid inlet and a fluid outlet and, contained in the vessel, an adsorbent comprising a surface and, linked with the surface, at least one hydrophobic member having 6 to 700 carbon atoms and further, linked with the surface or with the hydrophobic member or with both, at least one negative charge-producing member having no carbon atom or having 1 to 5 carbon atoms which negative charge-producing member produces such an effective number of negative charges in a body fluid that the ratio of:

$$\frac{\text{Effective number of negative charges}}{\text{Number of said hydrophobic members}}$$

is greater than 1.

DETAILED DESCRIPTION OF THE DRAWINGS

Turning now to FIG. 1 there is shown one form of the adsorbing device for an autoantibody and/or immune complexes according to the present invention. In this device, a cap 6 having a body fluid inlet 5 is screwed over one open end of a cylinder 2 through a packing 4 having a filter 3 spread on the inner side thereof and a cap 8 having a body fluid outlet 7 is screwed over the other open end of the cylinder 2 through a packing 4' having a filter 3' spread on the inner side thereof, and the adsorbent is packed and held between the filters 3 and 3' to form an immune adsorbent layer 9.

In the adsorbent layer 9, the adsorbent of the present invention alone may be contained, or, the layer 9 may be comprised of an adsorbent mixed with other adsorbents or the layer 9 may be comprised of at least one layer of the adsorbent of the present invention superimposed upon at least one other kind of adsorbent layer. As such other adsorbents, there can be used adsorbents for malignant substances (antigens) such as DNA and active charcoal having an adsorbing capacity in a broad range. In this case, the clinical effect attained can be expected to be in a broad range, because of the synergistic actions of the adsorbents. When the adsorbing device is used for ectosomatic circulation, it is preferred that the volume of the adsorbent layer 9 be about 50 to about 400 ml.

When the adsorbing device of the present invention is used for ectosomatic circulation, the following two methods are ordinarily adopted. According to one method, the blood taken out from the interior of the living body is separated into the plasma component and the hematocyte component by means of a centrifugal separator or membrane type plasma separator; the plasma component is passed through the adsorbing device to be thereby purified; and the purified plasma component is combined with the hematocyte component and returned to the interior of the living body. Hence, in a further aspect of the present invention, there is provided a blood purifying apparatus for adsorbing and removing an autoantibody and/or immune complexes from blood plasma, which comprises a blood introduction means, a purified blood discharge means, a blood circulation passage provided with a plasma separating means and a blood-plasma mixing means, and a plasma recycle passage having both ends connected respectively to intermediate portions of said blood circulation passage to introduce plasma, which is separated by the plasma separating means, into said mixing means through a plasma purifying means, said blood circulation passage running between said blood introduction means and said purified blood discharge means, and wherein said plasma purifying means comprises a vessel having a fluid inlet and a fluid outlet and, contained in the vessel, an adsorbent comprising a surface and, linked with the surface, at least one hydrophobic member having 6 to 700 carbon atoms and further, linked with the surface or with the hydrophobic member or with the both, at least one negative charge-producing member having no carbon atom or having 1 to 5 carbon atoms, said negative charge-producing member being adapted to produce such an effective number of negative charges in a body fluid that the ratio of:

$$\frac{\text{Effective number of negative charges}}{\text{Number of said hydrophobic members}}$$

is greater than 1.

According to the other method, the blood taken out from the interior of the living body is directly passed through the aforementioned adsorbing device so that the blood is purified.

The adsorbing capacity of the adsorbent of the present invention is so high that the grain size of the adsorbent can be increased, and that the packing ratio can be decreased. Hence, the body fluid such as blood and plasma can be passed through the adsorbent at a high rate, regardless of the shape of the adsorbent. For this reason, by the use of the adsorbent of the present invention, it is possible to purify a large amount of body fluid in a short time.

The body fluid may be circulated in a continuous manner or discontinuous manner according to clinical necessity or equipment conditions.

As is apparent from the foregoing, the adsorbent of the present invention can adsorb and thus remove an autoantibody and/or immune complexes from a body fluid in a highly selective and highly efficient manner. Therefore, by the use of the adsorbent of the present invention, it is possible to assemble a very compact adsorbing device for autoantibody and/or immune complexes which can be used easily and safely.

The adsorbent of the present invention can, in general, be used for purifying and regenerating a body fluid such as blood and plasma. It is especially useful for the ectosomatic circulation therapy of diseases such as cancer, immune proliferative syndrome, chronic rheumatoid arthritis, collagen diseases such as systemic erythematodes, autoimmune diseases such as severe myasthenia, diseases and phenomena concerned with immune reactions in the living body such as allergy and rejection reaction in transplantation of internal organs, kidney diseases such as nephritis and liver diseases such as hepatitis.

The present invention will now be described in detail with reference to the following Examples.

EXAMPLE 1

Various organic compounds, as indicated in Table 1, each having 2 or more negative charge-producing members and also having 6 or more carbon atoms were bonded to CNBr-activated Sepharose 4B (a CNBr-activated agarose gel, having an average particle diameter of 60 to 140 microns and a molecular weight exclusion limit of $2 \times 10^7$, which is manufactured and sold by Pharmacia Co., Sweden) by the customary method as will be explained below to obtain adsorbents for which the ratio of $$\frac{\text{Effective number of negative charges}}{\text{Number of hydrophobic members}}$$

is 2 or more.

Illustratively stated, 100 mg of each of the organic compouds as given in Table 1 was dissolved in 100 ml of 0.1 M carbonate buffer solution containing 0.5 M sodium chloride. To the resulting solution was added 5 ml of CNBr-activated Sepharose 4B. Reaction was effected at 4° C. overnight, and then the gel was taken out and put in 50 ml of 1 M aqueous ethanolamine. The gel was stirred at room temperature for two hours to block the remaining excessive active groups of the gel. Thus, there was obtained an adsorbent. In the manner as mentioned above, seven adsorbents (Adsorbents A to G) as shown in Table 1 were produced. The amount of the organic compound bonded to the CNBr-activated Sepharose 4B was determined as follows. The remaining primary amino groups of the organic compound was reacted with and bonded to 4-phenylspiro [furan-2(3 H)-1'-phthalan]-3,3'-dion ("Furlam®", manufactured by Hoffman La Roche & Co., Switzerland). The reaction product was subjected to the measurement with fluorescent rays of 475 to 490 nm (exciting waves: 390 nm) to determine the amount (A) of the organic compound adsorbed to the CNBr-activated Sepharose 4B. Separately, there was determined the amount (B) which had organic compound physically bonded to Sepharose 4B which had not been subjected to the activation treatment. The amount of the organic compund bonded to the CNBr-activated Sepharose 4B was calculated by subtracting the amount (B) from the 4B was calculated by subtracting the amount (B) from the amount (A). Using the above-prepared adsorbents, adsorption tests were effected as follows. Three volumes of an anticoagulant (sodium citrate)-added plasma of a patient suffering from rheumatoid arthritis was mixed with one volume of the above-prepared adsorbent and incubated at 37° C. for 3 hours. Then, the supernatant of the plasma mixture was subjected to determination with respect to rheumatoid factor, immune complexes, fibrinogen and immunoglobulin G.

The rheumatoid factor concentration was determined by the latex fixation test and the passive sensitized hematocyte agglutination test. When the polystyrene latex particles on which human γ-globulin has been adsorbed is reacted with the plasma of a patient having the rheumatoid factor, the fixation of latex particles is caused. In the latex fixation test, such a phenomenon is utilized for the detection of rheumatoid factor. More specifically, a series of dilutions of the above-obtained plasma with varied concentrations were prepared using a glycine-containing saline buffer solution, and the rheumatoid factor concentration was evaluated, based on the plasma dilution ratio at which the fixation of latex particles was not caused any more. In other words, the dilution ratio at which the rheumatoid factor became negative was determined. In the case of the plasma containing the rheumatoid factor at a high level, the dilution ratio at which the fixation became negative was increased, whereas, in the case of the plasma containing the rheumatoid factor at a low level, the dilution ratio at which the fixation became negative was lowered. Ihe latex fixation test was carried out by using a kit manufactured and sold by Nippon Toketsu Kanso Kenkysho, Japan.

In the passive sensitized hematocyte agglutination test, sheep erythrocytes on which rabbit γ-globulin had been adsorbed were used, and other procedures were the same as in the latex fixation test. The passive sensitized hamatocyte test was carried out by using a kit (RAHA test kit) manufactured and sold by Fuji Zoki Seiyaku K.K., Japan. It is generally considered that the specificity for the rheumatoid factor is higher in the passive sensitized hematocyte agglutination test than in the latex fixation test.

The immune complex concentration was determined in accordance with polyethylene glycol precipitation method. In this method, the immune complex precipitated and recovered by polyethylene glycol is determined by measuring the quantity of immunoglobulin according to the single radial immuno-diffusion method. In the single radial immuno-diffusion method an antigen (a protein to be determined) is put in a hole of an agar plate involving an antibody. An antigen-antibody reaction occurs in the hole of the agar plate. As a result, there is formed a ring-like precipitate of which the area is proportional to the concentration of the antigen. The concentration of the antigen is determined from the area of the ring-like precipitate. The detailed operation procedures and conditions of the method of determining the immune complex concentration will be described below.

(1) 1.0 ml of the sample was placed in a test tube. 1.0 ml of 8% polyethylene glycol (average molecular weight: 6,000–7,500) was added thereto and the resulting mixture was stirred. Then, the stirred mixture was allowed to stand at 4° C. for 60 minutes.

(2) The mixture was subjected to centrifugal separation at 4° C. under a load of 1,000 g for 60 minutes and the supernatant was removed. The obtained precipitates were dissolved in PBS (a phosphoric buffer physiological saline solution) to give 1.0 ml.

(3) The procedures of (1) and (2) were repeated twice to wash out the remaining monomeric immunoglobulin.

(4) The finally obtained suspension of immune complexes in PBS was subjected to determination of immunoglobulin G in accordance with the single radial immuno-diffusion method as described above.

Ihe fibrinogen concentration also was determined by the single radial immuno-diffusion method as described above. The plasma of a patient suffering from rheumatoid arthritis used in the above tests had a rheumatoid factor titer of 1,280 (in the latex test) and 5,120 (in the RAHA test), an immune complex concentration (based on the determination of immunoglobulin G) of 60 mg/dl, a fibrinogen concentration of 250 mg/dl and an immunoglobulin G concentration of 1,600 mg/dl.

The results of the above-described adsorption tests are shown in Table 1.

From the test results, it is apparent that the adsorbents of the present invention, viz. Adsorbents A to G of Table 1, are excellent in adsorbing capacity of the rheumatoid factor and immune complexes while adsorbing little fibrinogen and immunoglobulin G. In Table 1, the carbon atom contained in CNBr which is a reagent used for activation is also included in the number of carbon atoms of the hydrophobic member.

TABLE 1

| Adsorbents | Organic Compounds | Linked amount (mg/ml) | Number of carbon atoms in hydrophobic member | Ratio* | Rheumatoid factor | | Immune complexes (mg/dl) | Fibrinogen (mg/dl) | Immunoglobulin G (mg/dl) |
|---|---|---|---|---|---|---|---|---|---|
| | | | | | Latex | RAHA | | | |
| A | Disulfoxyaniline | 2.1 | 7 | 2 | 320 | 1,280 | 28 | 235 | 1,500 |
| B | 7-Amino-1,3-naphthalene disulfonic acid | 2.0 | 11 | 2 | 160 | 640 | 16 | 230 | 1,490 |
| C | Tyrosine-o-sulfuric acid ester | 1.9 | 9 | 2 | 320 | 1,280 | 28 | 235 | 1,510 |
| D | Acid red 37 (Aldrich Chemical Co., Ltd., U.S.A. | 1.8 | 19 | 2 | 160 | 640 | 16 | 235 | 1,500 |
| E | m-Carboxyphenylalanine | 2.2 | 9 | 2 | 320 | 640 | 20 | 240 | 1,510 |
| F | m-Carboxytyrosine | 2.0 | 9 | 2 | 320 | 1,280 | 24 | 230 | 1,490 |
| G | Succinocanavanine | 2.4 | 7 | 3 | 320 | 1,280 | 26 | 235 | 1,520 |
| | Plasma of a patient suffering from rheumatoid arthritis | — | — | — | 1,280 | 5,120 | 60 | 250 | 1,600 |

* $\frac{\text{Effective number of negative charges}}{\text{Number of hydrophobic members}}$

COMPARATIVE EXAMPLE 1

Adsorbents were prepared and tested in substantially the same manner as in Example 1, except that there were employed an organic compound, as shown in Table 2, having less than 6 carbon atoms and those having no negative charge-producing member. Incidentally, with respect to an organic compound of which the solubility in 0.1 M carbonate buffer is low, 100 ml of dimethyl sulfoxide was additionally used. The obtained results are shown in Table 2.

From the results shown in Table 2, it is seen that the adsorbents prepared using organic compounds having 5 or less carbon atoms in the hydrophobic member are low in the capacity of adsorbing the rheumatoid factor and immune complexes, and the adsorbents carrying no negative charge-producing member not only exhibit the lowered capacity of adsorbing the rheumatoid factor and immune complexes but also adsorb fibrinogen.

copolymer. The obtained copolymer was recovered by filtration, washed with water, extracted with acetone and subjected to an ester exchange reaction in a solution of 46.5 g of sodium hydroxide in 2 liters of methanol at 40° C. for 18 hours. The obtained gel had an average particle size of 150 μm, a vinyl alcohol unit per unit weight ($q_{OH}$) of 10.0 meq/g, a specific surface area of 60 m$^2$/g and a molecular weight exclusion limit (dextran) of $6 \times 10^5$.

Then, 10 g (on the dry basis) of the obtained gel was suspended in 120 ml of dimethyl sulfoxide. To the resulting suspension were added 8.3 ml of epichlorohydrin and 10 ml of 30% by weight sodium hydroxide solution. The mixture was stirred at 30° C. for 5 hours to effect an activation reaction. After completion of the reaction, the reaction product was washed with dimethyl sulfoxide, washed with water and then suction dehydrated to obtain the activated gel. The activated gel thus obtained was suspended in 160 ml of 0.1M sodium carbonate buffer (pH 9.8) containing 2.5 g of 7-amino-1,3-naphthalenedisulfonic acid and subjected

TABLE 2

| Adsorbent | Organic compounds | Linked amount (mg/ml) | Number of carbon atoms in hydrophobic member | Ratio* | Rheumatoid factor | | Immune complexes (mg/dl) | Fibrinogen (mg/dl) | Immunoglobulin G (mg/dl) |
|---|---|---|---|---|---|---|---|---|---|
| | | | | | Latex | RAHA | | | |
| H | Aspartic acid | 1.8 | 3 | 2 | 640 | 2,560 | 40 | 240 | 1,400 |
| I | Naphthylamine | 2.2 | 11 | 0 | 640 | 2,560 | 45 | 125 | 1,500 |
| J | 2-Aminoanthracene | 2.3 | 15 | 0 | 640 | 2,560 | 45 | 105 | 1,500 |
| | Plasma of a patient suffering from rheumatoid arthritis | — | — | — | 1,280 | 5,120 | 60 | 250 | 1,600 |

* $\frac{\text{Effective number of negative charges}}{\text{Number of hydrophobic members}}$

EXAMPLE 2

A homogeneous liquid mixture of 100 g of vinyl acetate, 52.0 g of triallyl isocyanurate (degree of crosslinking: 0.35), 100 g of ethyl acetate, 100 g of heptane, 7.5 g of polyvinyl acetate (polymerization degree: 500) and 3.8 g of 2,2'-azobisisobutyronitrile and 400 ml of water containing 1% by weight of polyvinyl alcohol, 0.05% by weight of sodium dihydrogenphosphate dihydrate and 1.5% by weight of disodium hydrogenphosphate dodecahydrate were charged in a flask, and the mixture was sufficiently stirred and heated with stirring at 65° C. for 18 hours and at 75° C. for 5 hours to effect suspension polymerization. There was obtained a granular to fixation reaction while stirring at 50° C. for 14 hours, followed by addition of 33 ml of 60.6 mg/ml tris(hydroxyethyl)aminomethane solution. In order to block the remaining active groups, the resulting mixture was kept at 50° C. for 5 hours while stirring. After 5 hours, the solid was recovered and then thoroughly washed with water to obtain an adsorbent for purifying a body fluid.

The amount of 7-amino-1,3-naphthalene-disulfonic acid fixed on the activated gel was 200 μmol/g (on the dry basis). The hydrophobic member fixed on the activated gel contained 13 carbon atoms and had a ratio

[(effective number of negative charges)/(number of hydrophobic members)] of 2.

The obtained adsorbent was packed in a column having an inner diameter of 30 mm and a length of 70 mm. Through the column was passed 150 ml of an anticoagulant (sodium citrate)-added plasma of a patient suffering from rheumatoid arthritis at a flow rate of 5 ml/min. In the test, there were observed no volume decrease of the adsorbent packed in the column, no clogging, no lowering in flow rate. The pressure loss between the inlet and the outlet of the column was 15 mmHg.

In the analysis of the plasma protein before and after passing the plasma through the column, it was found that the rheumatoid factor titer which was 320 in the latex test and 2,560 in the RAHA test before the plasma was passed through the column was decreased by passing the plasma through the column. The immune complex concentration [determined according to the Clq solid-phase EIA (Enzyme Immunoassay) method] was 20 μg/ml before the plasma was passed through the column, and the concentration was decreased to less than 3 μg/ml by passing the plasma through the column. On the other hand, the fibrinogen concentration and immunoglobulin G concentration were slightly decreased from 195 mg/dl to 180 mg/dl and from 1,320 mg/dl to 1,210 mg/dl, respectively.

EXAMPLE 3 AND COMPARATIVE EXAMPLE 2

The gel as obtained in Example 2 was used as a carrier. After activation with epichlorohydrin, each of the hydrophobic member compounds, as shown in Table 3, having 6 to 700 carbon atoms and each of the negative charge-producing member compounds, as shown in Table 3, having 5 or less carbon atoms were bonded to the carrier, and the active group remaining in excess were blocked with ethanolamine. The ratio of the effective number of negative charges to the number of hydrophobic members was controlled by varying the ratio of the hydrophobic member compound to the negative charge-producing member compound when they were bonded to the carrier. Thus, there were obtained the adsorbents having varied values in the ratio of the effective number of negative charges to the number of hydrophobic members. The total amount of the hydrophobic member compound and the negative charge-producing member compound bonded to the carrier was adjusted to about 50 μmol/ml of the gel. Of the above-obtained adsorbents, the adsorbents for which the ratio of the effective number of negative charges to the number of hydrohobic members is less than one or which has no hydrophobic member are the comparative tests.

Compounds used are summarized in Table 3.

TABLE 3

| Marks in FIGS. 2 through 6 | Negative charge-producing member compound having 5 or less carbon atoms which produces a negative charge in a body fluid | Hydrophobic member compound having 6 to 700 carbon atoms |
| --- | --- | --- |
|  | Sulfamic acid | Naphthylamine |
| X | Taurine | 2-Aminoanthracene |
| Δ | Glycine | Aniline |

In the adsorption test, 3 volumes of an anticoagulant (sodium citrate)-added plasma of a patient suffering from rheumatoid arthritis was mixed with 1 volume of the adsorbent. The mixture was incubated at 37° C. for 3 hours, and then the supernatant was subjected to determination of the rheumatoid factor, immune complexes, immunoglobulin G and fibrinogen. The plasma of a patient suffering from rheumatoid arthritis used in the tests had a rheumatoid factor titer of 320 (latex test) and 1,280 (RAHA test), an immune complex concentration (based on the determination of immunoglobulin G) of 50 mg/dl, an immunoglobulin G concentration of 1,600 mg/dl and a fibrinogen concentration of 230 mg/dl.

The results of the adsorption tests are shown in FIGS. 2 through 6. In the figures, the dotted lines are values for the patient plasma.

From the figures, it is seen that the adsorbents having both a hydrophobic member and a negative charge-producing member on the surface have a high capacity of adsorbing the rheumatoid factor and immune complexes. Moreover, it is also noted that the adsorbents for which the ratio of the effective number of negative charges to the number of hydrophobic members is greater than unity exhibit little or no adsorption of fibrinogen and immunoglobulin G.

EXAMPLE 4

The gel as obtained in Example 2 was used as a carrier. After activation with epichlorohydrin, poly-L-phenylalanine (number of carbon atoms in the hydrophobic member: 270–540, number of negative charges: 1) and taurine (number of carbon atoms: 2, number of negative charges: 1) were bonded simultaneously to the carrier. There was obtained an adsorbent for which the ratio of the effective number of negative charges to the number of hydrophobic members was 2.5 and in which the total amount of the poly-L-phenyl-alanine and taurine bonded to the carrier was 4 mg/ml of the gel.

The adsorption test was carried out in the same manner as in Example 3. The plasma of a patient suffering from rheumatoid arthritis used in the test had a rheumatoid factor titer of 320 (latex test) and 2,560 (RAHA test), an immune complex concentration (based on the determination of immunoglobulin G) of 43 mg/dl, an immunoglobulin G concentration of 1,300 mg/dl and a fibrinogen concentration of 230 mg/dl. After adsorption, the rheumatoid factor titer was decreased to 40 (latex test) and to 160 (RAHA test), and the immune complex concentration was decreased to 8 mg/dl. The immunoglobulin G concentration and the fibrinogen concentration were slightly decreased to 1,200 mg/dl and 200 mg/dl, respectively.

What is claimed is:

1. An adsorbent for adsorbing thereonto an autoantibody and/or immune complexes from a body fluid, which comprises a surface and, linked with the surface, at least one hydrophobic member having 6 to 700 carbon atoms and further, linked with the surface or with the hydrophobic member or with the both, at least one negative charge-producing member having no carbon atom or having 1 to 5 carbon atoms, said negative charge-producing member being adapted to produce such an effective number of negative charges in a body fluid that the ratio of:

$$\frac{\text{Effective number of negative charges}}{\text{Number of said hydrophobic members}}$$

is greater than 1.

2. An adsorbent according to claim 1, wherein said ratio is in the range of 1.1 to 10.

3. An adsorbent according to claim 2, wherein said ratio is in the range of 1.2 to 5.

4. An adsorbent according to claim 1 wherein said hydrophobic member is a compound comprising at least one aromatic ring.

5. An adsorbent according to claim 4, wherein said aromatic ring is a benzene ring or a fused benzene ring.

6. An adsorbent according to claim 1, wherein said negative charge-producing member is a carboxyl group or a sulfo group.

7. An adsorbent according to claim 1, wherein said negative charge-producing member is linked with the hydrophobic member as a substituent thereof, the number of said negative charge-producing members per hydrophobic member being 2 or more.

8. An adsorbent according to claim 1, wherein said surface is the surface of a carrier which is insoluble in the body fluid.

9. An adsorbent according to claim 8, wherein said carrier has a hydroxyl group.

10. An adsorbent according to claim 8, wherein said carrier is of a particle having an average particle diameter of 25 to 2,500 microns.

11. An adsorbent according to claim 8, wherein said carrier is of a fibrous form having a diameter of 0.02 to 10 denier.

12. An adsorbent according to claim 8, wherein said carrier is a crosslinked copolymer having a hydroxyl group.

13. An adsorbent according to claim 12, wherein said crosslinked copolymer is a crosslinked copolymer comprising vinyl alcohol units as the main constituent units.

14. An adsorbent according to claim 13, wherein said crosslinked copolymer comprising vinyl alcohol units as the main constituent units is a crosslinked polyvinyl alcohol obtained by hydrolyzing a copolymer of a vinyl ester of a carboxylic acid with a vinyl compound containing an isocyanurate ring.

15. An adsorbing device for an autoantibody and/or immune complexes from a body fluid, which comprises a vessel having a fluid inlet and a fluid outlet and, contained in the vessel, an adsorbent comprising a surface and, linked with the surface, at least one hydrophobic member having 6 to 700 carbon atoms and further, linked with the surface or with the hydrophobic member or with the both, at least one negative charge-producing member having no carbon atom or having 1 to 5 carbon atoms, said negative charge-producing member being adapted to produce such an effective number of negative charges in a body fluid that the ratio of:

$$\frac{\text{Effective number of negative charges}}{\text{Number of said hydrophobic members}}$$

is greater than 1.

16. A blood purifying apparatus for adsorbing and removing an autoantibody and/or immune complexes from blood plasma, which comprises a blood introduction means, a purified blood discharge means, a blood circulation passage provided with a plasma separating means and a blood-plasma mixing means, and a plasma recycle passage having both ends connected respectively to intermediate portions of said blood circulation passage to introduce plasma, which is separated by the plasma separating means, into said mixing means, through a plasma purifying means, said blood circulation passage running between said blood introduction means and said purified blood discharge means, and wherein said plasma purifying means comprises a vessel having a fluid inlet and a fluid outlet and, contained in the vessel, an adsorbent comprising a surface and, linked with the surface, at least one hydrophobic member having 6 to 700 carbon atoms and further, linked with the surface or with the hydrophobic member or with the both, at least one negative charge-producing member having no carbon atom or having 1 to 5 carbon atoms, said negative charge-producing member being adapted to produce such an effective number of negative charges in a body fluid that the ratio of:

$$\frac{\text{Effective number of negative charges}}{\text{Number of said hydrophobic members}}$$

is greater than 1.

* * * * *

UNITED STATES PATENT AND TRADEMARK OFFICE
CERTIFICATE OF CORRECTION

PATENT NO. : 4,627,915

DATED : December 9, 1986

INVENTOR(S) : Toru Kuroda, et al.

It is certified that error appears in the above-identified patent and that said Letters Patent is hereby corrected as shown below:

Title Page, "Title", line 1 and Column 1, line 1     Delete "ABSORBENT" and substitute --ADSORBENT--

Col. 12, lines 1 and 52     Delete "Ihe" and substitute --The--

Col. 15, line 59, Table 3     First line under "Marks in Figs. 2 through 6" and to left of "Sulfanic Acid" insert --O--

Title page, insert the following:

-- Foreign Patent Documents 0056977     8/82     Europe --

Signed and Sealed this

Eighteenth Day of October, 1988

*Attest:*

DONALD J. QUIGG

*Attesting Officer*     *Commissioner of Patents and Trademarks*